United States Patent [19]

Freitag

[11] Patent Number: 4,929,545
[45] Date of Patent: May 29, 1990

[54] METHOD AND REAGENT FOR DETERMINATION OF AN ANALYTE VIA ENZYMATIC MEANS USING A FERRICYANIDE/FERRIC COMPOUND SYSTEM

[75] Inventor: Helmut Freitag, Indianapolis, Ind.

[73] Assignee: Boehringer Mannheim Corporation, Indianapolis, Ind.

[21] Appl. No.: 339,051

[22] Filed: Apr. 14, 1989

[51] Int. Cl.$^5$ .............................................. C12Q 1/58
[52] U.S. Cl. ........................................ 435/11; 435/4; 435/14; 435/28
[58] Field of Search ............................ 435/11, 14, 28

[56] References Cited

U.S. PATENT DOCUMENTS 4,576,913  3/1986  Adachi et al. ...................... 435/26

Primary Examiner—Sam Rosen
Attorney, Agent, or Firm—Felfe & Lynch

[57] ABSTRACT

A composition useful in determining analytes, such as glucose or cholesterol, is disclosed. The composition contains an enzyme which specifically reacts with the analyte to be determined, a soluble ferricyanide compound which is reducible to form a ferrocyanide, a soluble ferric compound which provides ferric ions for reacting with ferrocyanide to form a reaction product, and a buffer which does not prevent formation of this reaction product. The composition has a pH of from about 3.0 to about 6.0.

23 Claims, No Drawings

METHOD AND REAGENT FOR DETERMINATION OF AN ANALYTE VIA ENZYMATIC MEANS USING A FERRICYANIDE/FERRIC COMPOUND SYSTEM

FIELD OF THE INVENTION

This invention relates to an enzymatic method for determining an analyte in a sample, and a reagent composition useful in this method. Of particular interests are methods and reagents useful in determining one of glucose and cholesterol.

BACKGROUND AND PRIOR ART

The central concern of clinical chemistry is the qualitative and quantitative determination of specific analytes in samples. Of special concern is the analysis of body fluid samples, such as blood, serum, urine, and so forth. Determination of the presence and/or amount of various analytes, followed by comparison to established parameters determines diagnosis of diseased or abnormal states.

The literature on analytical determination of body fluid samples is an enormous one, as the art has investigated the determination of, e.g., glucose, cholesterol, creatine, sarcosine, urea, and other substances in samples of blood, serum, urine, and so forth.

The early clinical literature taught various non-enzymometric methods for determining analytes. Exemplary of this are the early glucose determination tests taught by Kaplan and Pesce in Clinical Chemistry: Theory, Analysis And Correlation (Mosby, 1984), pages 1032–1042. Such tests include the reduction of copper ions, reaction of copper with molybdate, and so forth. As this reference points out, these methods are insufficiently accurate, due to poor specificity and interference by other analytes. One method described by Kaplan, et al. is the alkaline ferricyanide test. This method involves heating a solution containing glucose in the presence of ferricyanide, at alkaline conditions. The reaction:

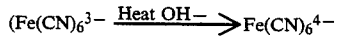

is accompanied by a change in color from yellow to colorless. Either this decrease in color is measured or the reaction of the colorless ferrocyanide ion with a ferric ion to form the intensely colored precipitate "Prussian Blue" is measured.

Formation of Prussian Blue is an essential part of the invention described herein, so this test will be referred to again, infra.

These early "chelation" type tests became replaced by more specific assays as enzymology became a more developed science. Enzymes are known for their extreme specificity, so via the use of an appropriate enzyme, the skilled artisan could determine, rather easily, whether or not a particular analyte is present, and how much. These enzymatic systems must be combined with indicator systems which, in combination with the enzyme reaction, form a detectable signal. Kaplan describes a glucose-hexokinase system, as well as a glucose oxidase system, and these are fairly well known to the art. They are used in connection with indicator systems such as the "coupled indicators" known as Trinder reagents, or oxidizable indicators such as o-tolidine and 3,3',5,5'-tetramethylbenzidine. In such systems, reaction of the enzyme with its substrate yields a surplus of electrons carried by the enzyme, which are removed by the indicator systems. Color formation follows, indicating presence, absence, or amount of analyte in the sample.

The patent literature is replete with discussions of such systems. A by no means exhaustive selection of such patents include 4,680,259, 4,212,938, 4,144,129 and 3,925,164 (cholesterol oxidase); 4,672,029, 4,636,464, 4,490,465 and 4,418,037 (glucose oxidase); and 4,614,714 (L-glutamic acid oxidase). All of these enzymatic systems "oxidize" their substrates (i.e., the analyte in question) in that they remove electrons therefrom.

Once the analyte loses its electrons, it plays no further part in the determination reaction. As indicated, supra, the electrons may be transferred into a color forming system, such as the Trinder system described in U.S. Pat. No. 4,291,121, or a tetrazolium system, such as is described in, e.g., U.S. Pat. No. 4,576,913.

Indicator systems are not the only means by which the captured electrons may be measured, however. Free electrons produce an electrical current, which can be measured as an indication of analyte. Such systems are described by, e.g., Schläpfer, et al., Clin. Chim. Acta 57: 283–289 (1974). These systems employ substances known as "mediators" which remove the electrons from the enzymes. Eventually, the mediators release the electrons as well, producing a measurable current as a result. These mediators can either absorb one, or two electrons per molecule of mediator. Ferricyanide, the preferred mediator described in the Schläpfer reference, picks up one electron per molecule of ferricyanide.

Electron mediators have been known and used in indicator systems in connection with so-called "dye molecules". The 4,576,913 patent, described supra, e.g., teaches the mediator phenazine methosulfate in combination with a tetrazolium salt. It is the latter which serves as the indicator. The use of these mediators enables one to proceed without oxygen. Normally, in a glucose determination reaction, oxygen is necessary to remove electrons from the reduced enzyme. This produces hydrogen peroxide:

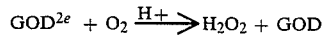

with the hydrogen peroxide taking part, in the presence of peroxidase, in reactions leading to formation of a color.

It is sometimes undesirable to use oxygen, or aerobic systems, because of various problems inherent in such systems. For example, in these reactions, the reaction is dependent on the partial pressure of $O_2$ in the atmosphere. In addition, because the $O_2$ must permeate throughout the entire test medium, the design of such media must be adapted to permit such permeatron. There is interest, then, in indicator systems which are anaerobic, such as those where a mediator is used in connection with the indicator, or electrochemical systems using the mediator alone.

Electrochemical systems, while useful, are not always practical for frequent testing at the present time, and, in terms of home use, individuals who must measure glucose levels daily, are accustomed to systems where a color change is used. Therefore, there exists a need for anaerobic systems which utilize indicator reactions producing a detectable signal, such as a color.

While indicator systems of the type described supra are available, there is a difficulty with these in that the indicator molecules themselves are frequently unstable and do not have long shelf lives. There is therefore an interest in systems which utilize stable molecules which can form a detectable signal.

It will be recalled that Kaplan taught the formation of Prussian Blue in glucose determination, but dismissed it as a viable alternative because of the lack of specificity. Apart from this, the severe conditions under which the reaction are taught to take place are totally unsuitable for enzymatic assays. The reaction Kaplan teaches requires boiling the solution. Enzymes are protein molecules, and inactivation via denaturing is characteristic of what happens when proteins are boiled. Thus, the skilled artisan, seeing the heat parameters of Kaplan would avoid this teaching for enzymatic assays.

Mention of the Prussian Blue system is found in the aforementioned U.S. Pat. No. 4,576,913. This patent teaches a glycerol dehydrogenase which operates in a fashion similar to oxidases in that it teaches removal of two electrons from its substrate molecule. Column 5 of the patent refers to the Prussian Blue system (referred to as "Berlin Blue") as an indicator.

This patent, however, must be read as a whole, and especially its teaching about the enzyme's operability. Enzymes are extremely pH sensitive, and the enzyme of the Adachi patent is said to operate in a pH range from 6.0 to 10.0, and optimally at 7.0 to 8.5. The teachings, therefore, would suggest to the artisan that since the glycerol dehydrogenase operates at alkaline pHs, the adaptation of the Prussian Blue system to enzyme detection would be at alkaline pHs. However, ferric salts precipitate at alkaline pHs, which would eliminate them from participating in a reaction to form Prussian Blue under the conditions Adachi describes as necessary.

The inventor has now found, quite surprisingly, that enzymatic assays can be performed using the formation of Prussian Blue. These assays do not involve the use of parameters which risk inactivation of the enzyme, such as high heat. The invention is based upon the discovery that, upon addition of sample to a reagent combination containing an enzyme, such as glucose oxidase or cholesterol oxidase, a ferricyanide salt, and a ferric salt buffered at a pH below which the enzyme is expected to be inactivated, the enzyme reactions nonetheless take place, and the buffer does not interfere with the reaction of ferrocyanide and $Fe^{3+}$.

Hence it is an object of this invention to provide a reagent composition useful in determining an analyte in a sample, which comprises an enzyme specific for the analyte to be determined, a ferricyanide compound, and a soluble ferric compound, wherein the reagent composition is at a pH below 7.

It is a further object of the invention to provide apparatus, such as test strips which can be used to determine an analyte which incorporate into reagent carriers the above described reagent composition.

Yet another object of this invention is to provide a method for determination of an analyte, comprising contacting a sample to the reagent composition described supra, and measuring formation of Prussian Blue, i.e., the complex of ferrocyanide and ferric ions as a measure of said analyte.

As has been described, this invention is based on the starting and unexpected finding that the ferricyanide/ferric salt system is operable at acidic pH, and under conditions where the enzyme being used would normally be inactive.

How the aforementioned objects of this invention are achieved will be seen in the following Detailed Description of Preferred Embodiments.

DETAILED DESCRIPTION OF PREFERRED EMBODIMENTS

In its simplest form, the invention is a reagent composition for determining an analyte, which comprises an enzyme which specifically reacts with the analyte to be determined, a soluble ferricyanide ion containing compound which, in the presence of a free electron, is reduced to a ferrocyanide ion containing compound, a soluble ferric ion containing compound which reacts with the ferrocyanide ion containing compound to form a reaction product, and a buffer which does not prevent reaction between said ferrocyanide and ferric ions, wherein the composition has a pH from about 3.0 to about 6.0. Especially preferred is a pH of from about 3.9 to about 4.6.

By an enzyme "which specifically reacts with an analyte to be determined", the skilled artisan recognizes that the enzyme reacts with the analyte being determined, to the exclusion of others. For example, glucose oxidase specifically reacts with glucose.

A "soluble ferricyanide containing compound" refers to a compound which is soluble in the fluid sample being analyzed, and which contains the well known ferricyanide ion. When dissolved in the sample, the ferricyanide ion become available for reduction by a free electron to form ferrocyanide ions.

A "soluble ferric compound" similarly, means a compound which dissolves in the sample, freeing ferric ions. These ions then react with the above mentioned ferrocyanide ions to form a reaction product.

The buffer "does not prevent" the reaction between ferrocyanide and ferric ions, meaning that, although it may indeed compete for reactions therewith, this competition is not sufficient to prevent formation of the reaction product referred to supra.

If a quantitative test is desired, the ferricyanide containing compound should be present at least in an amount sufficient to accept all of the electrons donated by a substrate/analyte molecule in its reaction with the specific enzyme. Most analytes, in, e.g., biological samples, are present in a defined range. Knowledge of this range, which can be ascertained, e.g., from *The Merck Manual* or *Diagnostic Tests Handbook* or any of the numerous clinical chemistry references available to the artisan. One uses an amount of ferricyanide in excess of the amount necessary to react with all of the particular analyte at the top of the maximum range in a given sample. Similarly, the amount of ferric compound to be present can be calculated fairly easily, as the ferric and terrocyanide ions react 1:1 molar basis. Precise amounts of reagents are not required, however, when one is performing an assay to determine a general range of analyte, or is performing a "yes/no" test.

The choice of ferricyanide and ferric compounds available to the artisan is a wide one, the only constraint being that they be soluble in the test sample. Examples of the salts which may be used are potassium ferricyanide and ferric chloride, although others will be known to the skilled artisan, the only constraints upon the choice being those described supra. The pH range recited supra may be maintained, e.g., via the use of an appropriate buffer. The preferred buffer is 4-amino butyric acid, although as long as the buffer operates in the recited range, and does not chelate the ferric ion to a degree that reaction with ferrocyanide is inhibited, any buffer will be suitable.

The enzyme chosen will, of course, depend upon the analyte to be detected. Of particular interest are glucose determination tests, where the enzyme used is glucose oxidase. Other enzyme systems may be used, and it is well within the skill of the art to determine if, in fact they are operable within the recited pH range.

The reagent composition may be used in the form of a solution, e.g., or a lyophilizate, a tablet, and so forth. Further, the reagent may be used in the form of a kit, where the individual components are kept in separate containers to be combined just prior to use.

The reagent composition may also be applied to products such as test strips. In such situations, the reagents are impregnated or incorporated into carrier materials such as fleece, films, and so forth. A detailed roster of these is not given there, as the art is quite familiar with the test carrier literature and the many available options.

The ferrocyanide/ferric ion complex, as described supra, is a heavy, intensely colored material which precipitates out of solution. In view of this, it is desirable, though not necessary, to incorporate into the reagents and test carriers components such as surface active agents which keep the precipitate in solution or additives which modify the color somewhat to ease its intensity. The inert white pigment $TiO_2$ is especially preferred for this.

Carrying out the method of this invention is quite simple. The test sample blood, serum, urine, etc., is mixed with the reagent, regardless of its form, and one observes formation of the ferrocyanide/ferric complex or lack thereof.

The following examples demonstrate the operability of the invention although they are not to be read as being in any way limitative of the broad disclosure contained herein.

EXAMPLE 1

A buffered solution was prepared via dissolving 60 mmoles of 4-amino butyric acid in 50 ml of water, together with 1.8 mmoles of ferric sulfate. The pH was adjusted to 4.0 using 1N $H_2SO_4$.

Thirty kU of glucose oxidase was added, together with 20 mmoles of $K_3[Fe(CN)_6]$, and water to obtain a final volume of 100 ml. This solution is referred to hereafter as "solution A".

One ml of solution A was then combined with 50 ul of one of (i) distilled water; (ii) 6 mM glucose solution or (iii) 600 mM glucose solution. Color formation was then observed as follows:

TABLE 1

| Test Solution | Solution A |
|---|---|
| Water | NONE |
| 6 mM glucose | slight blue color |
| 600 mM glucose | heavy blue color. |

EXAMPLE 2

The effect of pH on the test systems of the invention was examined. To do so, solutions were prepared which contained 200 mM of 4-amino butyric acid, 20 mM ferric sulfate, 80 mM $K_3[Fe(CN)_6]$, and 450 U glucosr oxidase/ml. The pH of the solutions were adjusted as indicated, using either 4N $H_2SO_4$ or 4N KOH.

To test the pH effect, a glucose solution was added in each solution with a different pH to give a final concentration of 7.1 mg/dl of glucose, and color formation was observed after 1 minute. This was compared to a control, which was read after fifteen minutes. The degree of color formation is indicated via the number of plus signs in the following Table 2.

TABLE 2

| pH | Control | Sample |
|---|---|---|
| 3.05 | + + | + |
| 3.30 | + | + + + + + + |
| 3.60 | + | + + + + + + |
| 3.92 | − | + + + + + |
| 4.32 | − | + + + + |
| 4.50 | − | + + |
| 4.80 | − | + |
| 5.20 | − | + |

This experiment shows that the invention operates over a range of pHs from about 3.0 to about 6.0. The preferred range is a pH of from about 3.3 to about 4.5. In a particular embodiment of the invention, a pH of from about 3.9 to about 4.0 is preferred.

The excellent results obtained at the low pHs are quite surprising in view of the teaching of the art regarding the operability of enzymes at different pHs. Bergmeyer, *Methods of Enzymatic Analysis*, Vol VI, at page 180, for example, teaches the pH optimum of glucose oxidase is 5.6.

EXAMPLE 3

Test strips were prepared and used in order to show the use of the invention in reflectance assays.

A coating mass was prepared which contained, per kilogram of the coating mass, 30 g. 4-amino butyric acid, 3.9g of ferric sulfate, 36g of ferricyanide salt, and 1000 ku of glucose oxidase. Nonreactive ingredients which made up the remainder of the mass included $TiO_2$ as a white pigment, TWEEN-20, (nonionic surfactant), PROPIOFAN-70D (film former) and NATROSOL (swelling agent). The pH of this mass was 4.1.

The mass was coated onto a clear, polyester foil of 100 um thickness, and was allowed to form a coating. The thickness of the coating was 150 um.

Glucose solution of various concentrations were applied to the films, which were evaluated one minute thereafter in a reflectance photometer (Macbeth), following standard protocols well known to the art. The percentage of reflectance for each solution was measured at 660 nanometers. The results are presented in Table 3:

TABLE 3

| GLUCOSE CONCENTRATION (mg/dl) | % RELFECTANCE |
|---|---|
| 0 | 78.46 |
| 50 | 63.93 |
| 100 | 54.03 |
| 150 | 48.40 |
| 230 | 41.82 |
| 300 | 37.63 |
| 400 | 33.72 |

The values obtained show that the percentage of reflectance decreases as the concentration of the analyte being measured (glucose) increases. As such, the system is functional in test strip form, using reflectance photometry.

EXAMPLE 4

Experiments were carried out to test the invention in connection with the enzyme cholesterol oxidase.

A test solution was prepared which contained 50 mM $K_3[Fe(CN)_6]$, 2.5 mM $FeCl_3$, and 50 mM 4-aminobutyric acid per liter, and which had a pH of 4.0.

Cholesterol oxidase was then added to a control sample, and a sample to the above test solution which also contained 100 mg/dl of cholesterol. The cholesterol oxidase was present at a concentration of 2 u/ml of sample.

The samples were then evaluated in a photometer to determine if there was a change in absorbance, and if so, how much. The values obtained are presented in Table 4.

TABLE 4

| Cholesterol concentration (mg/dl) | absorbance change after 1 minute |
|---|---|
| 0 | 0.012 |
| 100 | 0.355 |

The control value is used for calibrating the assay, as will be recognized by the skilled artisan. The change in absorbance with the cholesterol concentration shows that the invention can be used with cholesterol oxidase.

The foregoing examples show the operation of the invention at various pHs and reagent formulations, using diverse enzymes. It has been shown that formulations including solutions and test strips can be used to carry-out the invention. The skilled artisan will note the easy adaptability of the system to include, e.g., powdered formulations or formulations where, e.g., the enzyme is immobilized on an inert bead or other type of carrier, with contact by the other components o& the reagent formulation.

The skilled artisan will note as well that formulations such as reagent kits can also be prepared. Reagent kits contain the elements of the invention, e.g., the enzyme, the ferricyanide and ferric salts and the buffer in separated containers. These containers are in turn encompassed by a container means which holds all of them, such as a box or rack. The separated components can be presented as solutions, powders, lyophilizates, impregnated on carriers, and so forth, or in any of the other reagent formulations recognized by the art.

In practice, the invention is of course used by contacting a liquid sample, such as blood, serum, urine, and so forth to the reagent composition. Formation of the Prussian Blue complex is measured as an indication of the analyte being assayed. This methodology does not vary, regardless of what form the composition takes, which includes it formulation as an analytical element or test strip, as described herein.

It will be understood that the specification and examples are illustrative but not limitative of the present invention and that other embodiments within the spirit and scope of the invention will suggest themselves to those skilled in the art.

I claim:

1. Composition useful in determining an analyte in a sample, comprising:
   (a) an enzyme which specifically reacts with said analyte;
   (b) a soluble ferricyanide compound which is reducible in the presence of an electron to produce a ferrocyanide compound;
   (c) a soluble ferric compound which reacts with a ferrocyanide compound to form a reaction product therebetween, and
   (d) a buffer which does not prevent formation of said reaction product, wherein said composition has a pH of from about 3.0 to about 6.0.

2. Composition of claim 1, wherein said enzyme is glucose oxidase.

3. Composition of claim 1, wherein said enzyme is cholesterol oxidase.

4. Composition of claim 1, wherein said buffer is 4-amino butyric acid.

5. Composition of claim 1, wherein said composition has a pH of from about 3.9 to about 4.6.

6. Composition of claim 1, wherein said composition has a pH of from about 3.9 to about 4.2.

7. Composition of claim 1, in the form of a solution which further comprises distilled water.

8. Composition of claim 1, in the form of a powder.

9. Composition of claim 1, wherein said soluble ferricyanide compound is potassium ferricyanide.

10. Composition of claim 1, wherein said soluble ferric compound is ferric chloride or ferric sulfate.

11. Composition of claim 1, impregnated onto a carrier.

12. Composition of claim 1, in lyophilized form.

13. Composition of claim 1 in the form of a kit comprising separate containers of each of said enzyme, said soluble ferricyanide compound, said soluble ferric compound and said buffer, and a container means for holding said separate containers.

14. Method for determining an analyte in a sample comprising a liquid sample containing an analyte which reacts with the enzyme of the composition of claim 1 and determining formation of said reaction product as a measure of said analyte.

15. Method of claim 14, wherein said sample is a body fluid sample.

16. Method of claim 14, wherein said analyte is glucose.

17. Method of claim 14, wherein said analyte is cholesterol.

18. Method for determining presence of an analyte in a liquid sample comprising contacting a liquid sample to the composition of claim 1, wherein said composition contains an enzyme which reacts with said analyte and determining formation of said reaction product, wherein formation of said reaction product is indicative of presence of said analyte in said sample.

19. Analytical element useful in determining an analyte in a sample, comprising:
   (a) a support carrier;
   (b) a reagent layer applied to said support carrier, said reagent layer comprising (i) an inert film, (ii) an enzyme which specifically reacts with said analyte, (iii) a soluble ferricyanide compound which is reduced in the presence of an electron to a ferrocyanide compound, (iv) a soluble ferric compound which reacts with said ferrocyanide compound to form a reaction product, and (v) a buffer which does not prevent formation of said reaction product, wherein said reagent layer has a pH of from about 3.0 to about 6.0.

20. Analytical element of claim 19, further comprising a nonionic detergent.

21. Analytical element of claim 19, further comprising an inert pigment.

22. Analytical element of claim 19, having a pH of from about 3.9 to about 4.6.

23. Analytical element of claim 19, having a pH of from about 3.9 to about 4.2.

* * * * *